US008039616B2

(12) United States Patent
Dennison et al.

(10) Patent No.: US 8,039,616 B2
(45) Date of Patent: Oct. 18, 2011

(54) BENZODIAZEPINE DERIVATIVES FOR TREATING HEPATITIS C INFECTION

(75) Inventors: Helena Dennison, London (GB); Justin Warne, London (GB); Keith Spencer, London (GB); George Cockerill, London (GB); James Lumley, London (GB)

(73) Assignee: AstraZeneca AB, Sodertalje (SE)

( * ) Notice: Subject to any disclaimer, the term of this patent is extended or adjusted under 35 U.S.C. 154(b) by 526 days.

(21) Appl. No.: 12/067,318

(22) PCT Filed: Sep. 19, 2005

(86) PCT No.: PCT/GB2005/003597
§ 371 (c)(1),
(2), (4) Date: Mar. 19, 2008

(87) PCT Pub. No.: WO2007/034127
PCT Pub. Date: Mar. 29, 2007

(65) Prior Publication Data
US 2009/0318427 A1 Dec. 24, 2009

(51) Int. Cl.
C07D 243/12 (2006.01)
A61K 31/55 (2006.01)
(52) U.S. Cl. ........................ 540/504; 514/221
(58) Field of Classification Search .................. 514/221; 540/504
See application file for complete search history.

(56) References Cited

U.S. PATENT DOCUMENTS

| 3,344,136 | A | | 9/1967 | Bell et al. |
| 4,628,084 | A | | 12/1986 | Bock et al. |
| 4,820,834 | A | * | 4/1989 | Evans et al. ................... 540/504 |
| 5,633,251 | A | * | 5/1997 | Claremon et al. ............ 514/221 |
| 5,852,010 | A | | 12/1998 | Graham et al. |
| 2002/0142940 | A1 | | 10/2002 | Graham et al. |

FOREIGN PATENT DOCUMENTS

| EP | 0 491 218 A1 | 6/1992 |
| EP | 0167919 B1 | 5/1993 |
| EP | 0284256 B1 | 6/1994 |
| WO | 93/17011 A1 | 9/1993 |
| WO | 95/14471 A1 | 6/1995 |
| WO | 95014694 A1 | 6/1995 |
| WO | 97/36879 A1 | 10/1997 |
| WO | 98/24805 A1 | 6/1998 |
| WO | 0004900 A1 | 2/2000 |
| WO | 00/12547 A2 | 3/2000 |
| WO | 00/66106 A2 | 11/2000 |
| WO | 01/00611 A1 | 1/2001 |
| WO | 01/74783 A1 | 10/2001 |
| WO | 01/90084 A1 | 11/2001 |
| WO | 01/92235 A1 | 12/2001 |
| WO | 03/015703 A2 | 2/2003 |
| WO | 03061632 A1 | 7/2003 |
| WO | 2004/026843 A1 | 4/2004 |
| WO | 2005/089770 A1 | 9/2005 |
| WO | 2005090319 A1 | 9/2005 |

OTHER PUBLICATIONS

Bock et al; Development of 1,4-Benzodiazepine Cholecystokinin Type B Antagonists, Journal of Medicinal Chemistry, 1993, pp. 4276-4292, vol. 36 (26).
Butcher et al; Preparation of 3-amino-1,4-benzodiazepin-2-ones via direct azidation with trisyl azide, Tetrahedron Letters, 1996, pp. 6685-6688, vol. 37, No. 37.
Evans et al; Methods for Drug Discovery: Development of potent, selective, orally effective cholecystokinin antagonists, Journal of Medicinal Chemistry, 1988 pp. 2235-2246 vol. 31, No. 12.
Haradahira et al; Synthesis and Evaluation of 11C-Labeled Nonpeptide Antagonists for Cholecystokinin Receptors: [11C]L-365,260 and [11C]L-365,346, Nuclear Medicine and Biology, 1998, 25(3), 203-208.

(Continued)

Primary Examiner — Shengjun Wang

(57) ABSTRACT

Use of a benzodiazepine of formula (I), or a pharmaceutically acceptable salt thereof, in the manufacture of a medicament for use in treating or preventing a hepatitis C infection, wherein: —$R^1$ represents $C_{1-6}$ alkyl, aryl or heteroaryl; —$R^2$ represents hydrogen or $C_{1-6}$ alkyl; —each $R^3$ is the same or different and represents halogen, hydroxy, $C_{1-6}$ alkyl, $C_{1-6}$ alkoxy, $C_{1-6}$ alkylthio, $C_{1-6}$ haloalkyl, $C_{1-6}$ haloalkoxy, amino, mono($C_{1-6}$ alkyl)amino, di($C_{1-6}$ alkyl)amino, nitro, cyano, —$CO_2R'$, —CONR'R", —NH—CO—R', —S(O)R', —S(O)$_2$R', —NH—S(O)$_2$R', —S(O)NR'R" or —S(O)$_2$NR'R", wherein each R' and R" is the same or different and represents hydrogen or $C_{1-6}$ alkyl; —n is from 0 to 3; —$R^4$ represents hydrogen or $C_{1-6}$ alkyl; —$R^5$ represents $C_{1-6}$alkyl, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-($C_{1-6}$ hydroxyalkyl)-, heteroaryl-($C_{1-6}$hydroxyalkyl)-, carbocyclyl-($C_{1-6}$ hydroxyalkyl)-, heterocyclyl-($C_{1-6}$hydroxyalkyl)-, aryl-C(O)—C(O)—, heteroaryl-C(O)—C(O)—, carbocyclyl-C(O)—C(O)—, heterocyclyl-C(O)—C(O)— or —$XR^6$; —X represents —CO—, —S(O)— or —S(O)$_2$—; and —$R^6$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-($C_{1-6}$ alkyl)-O—, heteroaryl-($C_{1-6}$ alkyl)-O—, carbocyclyl-($C_{1-6}$ alkyl)-O—, heterocyclyl-($C_{1-6}$ alkyl)-O— or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)-, heteroaryl-($C_{1-6}$ alkyl)-, carbocyclyl-($C_{1-6}$ alkyl)- or heterocyclyl-($C_{1-6}$ alkyl)-.

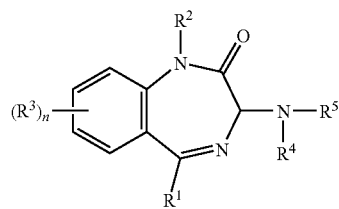

(I)

4 Claims, No Drawings

OTHER PUBLICATIONS

Rawson et al; Stereochemistry of the Benzodiazepine Based RAS Farnesyltransferase Inhibitors, Bioorganic and Medicinal Chemistry Letters, 1995, 5 (13):1335-1338.

Reider et al; Crystallization-induced asymmetric transformation: stereospecific synthesis of a potent peripheral CCK antagonist, Journal of Organic Chemistry, 1987 pp. 955-957 vol. 52.

Shi et al; Crystallization-induced asymmetric transformation: stereospecific synthesis of L-768,673, Tetrahedron, 1999 pp. 909-918 vol. 55, No. 4.

Search report citing: Giudice, et al; Synthesis of 2- and 3- amino-1,4-benzodiazepines, Farmaco, Edizione Scientifica (1982), 37(5), 343-52.

* cited by examiner

BENZODIAZEPINE DERIVATIVES FOR TREATING HEPATITIS C INFECTION

CROSS-REFERENCE TO RELATED APPLICATIONS

This application is a US National Stage under 35 U.S.C §371 of International Application No. PCT/GB2005/003597 (filed Sep. 19, 2005).

The present invention relates to a series of anti-viral benzodiazepine derivatives. In particular, it relates to a series of benzodiazepine derivatives which are active against the hepatitis C virus (HCV).

WO 04/026843 discloses a series of benzodiazepine derivatives which inhibit RSV replication. It is a finding of the invention that the compounds disclosed in WO 04/026843 are also active against HCV.

The present invention therefore provides the use of a benzodiazepine of the formula (I), or a pharmaceutically acceptable salt thereof, in the manufacture of a medicament for use in treating or preventing an HCV infection.

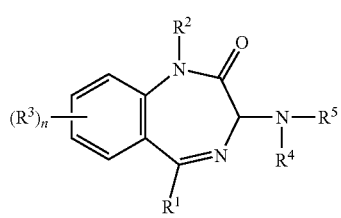

(I)

wherein:
$R^1$ represents $C_{1-6}$ alkyl, aryl or heteroaryl;
$R^2$ represents hydrogen or $C_{1-6}$ alkyl;
each $R^3$ is the same or different and represents halogen, hydroxy, $C_{1-6}$ alkyl, $C_{1-6}$ alkoxy, $C_{1-6}$ alkylthio, $C_{1-6}$ haloalkyl, $C_{1-6}$ haloalkoxy, amino, mono($C_{1-6}$ alkyl)amino, di($C_{1-6}$ alkyl)amino, nitro, cyano, —$CO_2R'$, —$CONR'R''$, —NH—CO—R', —S(O)R', —S(O)$_2$R', —NH—S(O)$_2$R', —S(O)NR'R'' or —S(O)$_2$NR'R'', wherein each R' and R'' is the same or different and represents hydrogen or $C_{1-6}$ alkyl;
n is from 0 to 3;
$R^4$ represents hydrogen or $C_{1-6}$ alkyl;
$R^5$ represents $C_{1-6}$ alkyl, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-C(O)—C(O)—, heteroaryl-C(O)—C(O)—, carbocyclyl-C(O)—C(O)—, heterocyclyl-C(O)—C(O)— or —$XR^6$.
X represents —CO—, —S(O)— or —S(O)$_2$—; and
$R^6$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-($C_{1-6}$ hydroxyalkyl)-, heteroaryl-($C_{1-6}$ hydroxyalkyl)-, carbocyclyl-($C_{1-6}$ hydroxyalkyl)-, heterocyclyl-($C_{1-6}$ hydroxyalkyl)-, aryl-($C_{1-6}$ alkyl)-O—, heteroaryl-($C_{1-6}$ alkyl)-O—, carbocyclyl-($C_{1-6}$ alkyl)-O—, heterocyclyl-($C_{1-6}$ alkyl)-O— or —NR'R'' wherein each R' and R'' is the same or different and represents hydrogen, $C_{1-6}$ alkyl, carbocyclyl, heterocyclyl, aryl, heteroaryl, aryl-($C_{1-6}$ alkyl)-, heteroaryl-($C_{1-6}$ alkyl)-, carbocyclyl-($C_{1-6}$ alkyl)- or heterocyclyl-($C_{1-6}$ alkyl)-.
Typically, R' and R'' are not both hydrogen.

As used herein, a $C_{1-6}$ alkyl group or moiety is a linear or branched alkyl group or moiety containing from 1 to 6 carbon atoms, such as a $C_{1-4}$ alkyl group or moiety. Examples of $C_{1-4}$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

As used herein, a hydroxyalkyl group is typically a said alkyl group that is substituted by one or more hydroxy groups. Typically, it is substituted by one, two or three hydroxy groups. Preferably, it is substituted by a single hydroxy group. Preferred hydroxyalkyl groups are (monohydroxy)ethyl groups.

As used herein, an acyl group is a $C_{2-7}$ acyl group, for example a group —CO—R, wherein R is a said $C_{1-6}$ alkyl group.

As used herein, an aryl group is typically a $C_{6-10}$ aryl group such as phenyl or naphthyl. Phenyl is preferred. An aryl group may be unsubstituted or substituted at any position. Typically, it carries 0, 1, 2 or 3 substituents.

Suitable substituents on an aryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —CONR'R'', —S(O)R', —S(O)$_2$R', —S(O)NR'R'', —S(O)$_2$NR'R''—NH—S(O)$_2$R' or —NH—CO—R', wherein each R' and R'' is the same or different and represents hydrogen or $C_{1-6}$ alkyl. Examples of suitable substituents on an aryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —CONR'R'', —S(O)R', —S(O)$_2$R', —S(O)NR'R'', —NH—S(O)$_2$R' or —NH—CO—R', wherein each R' and R'' is the same or different and represents hydrogen or $C_{1-6}$ alkyl.

Preferred substituents on an aryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, amino, mono($C_{1-6}$ alkyl)amino, di($C_{1-6}$ alkyl)amino, nitro, cyano, —$CO_2R'$, —S(O)R', —S(O)$_2$R' and —S(O)$_2$NR'R'', wherein each R' and R'' is the same or different and represents hydrogen or $C_{1-4}$ alkyl. Examples of preferred substituents on an aryl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$alkyl)amino, di($C_{1-6}$ alkyl)amino, nitro and cyano.

Particularly preferred substituents include fluorine, chlorine, bromine, iodine, $C_{1-4}$ alkyl, $C_{2-4}$ acyl, hydroxy, $C_{1-4}$ alkoxy, $C_{1-4}$ alkylthio, $C_{1-4}$ haloalkyl, $C_{1-4}$ haloalkoxy, amino, mono($C_{1-4}$ alkyl)amino, di($C_{1-4}$ alkyl)amino, nitro, —$CO_2R'$, —S(O)$_2R'$ and —S(O)$_2NH_2$, wherein R' represents $C_{1-2}$ alkyl. Examples of particularly preferred substituents include fluorine, chlorine, bromine, $C_{1-4}$ alkyl, $C_{1-4}$ alkoxy, $C_{1-4}$ haloalkyl and nitro.

As used herein, references to an aryl group include fused ring systems in which an aryl group is fused to a monocyclic carbocyclyl, heterocyclyl or heteroaryl group or to a fused group which is a monocyclic carbocyclyl, heterocyclyl or heteroaryl group which is fused to a phenyl ring. Typically, said fused ring systems are systems in which an aryl group is fused to a monocyclic carbocyclyl, heterocyclyl or heteroaryl group. Preferred such ring systems are those wherein an aryl group is fused to a fused group which is a monocyclic heterocyclyl or heteroaryl group or to a monocyclic carbocyclic group fused to a phenyl ring, in particular those wherein an aryl group is fused to a heterocyclyl or heteroaryl group.

Examples of such fused ring systems are groups in which a phenyl ring is fused to a thienyl group or to a tetrahydrofuranyl group to form a benzothienyl or dihydrobenzofuranyl group. Further examples of such fused rings are groups in which a phenyl ring is fused to a dioxanyl group, a pyrrolyl group or a 2,3-dihydroinden-1-one group to form a benzodioxinyl, indolyl or a 9H-fluoren-9-one group.

As used herein, a carbocyclyl group is a non-aromatic saturated or unsaturated monocyclic hydrocarbon ring, typically having from 3 to 6 carbon atoms. Preferably it is a saturated hydrocarbon ring (i.e. a cycloalkyl group) having from 3 to 6 carbon atoms. Examples include cyclopropyl, cyclobutyl, cyclopentyl and cyclohexyl. It is preferably cyclopentyl or cyclohexyl. A cycloalkyl group may be unsubstituted or substituted at any position. Typically, it carries 0, 1, 2 or 3 substituents.

Suitable substituents on a carbocyclyl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, oxo, —$CO_2R'$, —$CONR'R''$, —$S(O)R'$, —$S(O)_2R'$, —$S(O)NR'R''$, —$S(O)_2NR'R''$, —NH—$S(O)_2R'$ or —NH—CO—R', wherein each R' and R" is the same or different and represents hydrogen or $C_{1-6}$ alkyl. Examples of suitable substituents on a carbocyclyl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —$CONR'R''$, —$S(O)R'$, —$S(O)_2R'$, —$S(O)NR'R''$, —NH—$S(O)_2R'$ or —NH—CO—R', wherein each R' and R" is the same or different and represents hydrogen or $C_{1-6}$ alkyl.

Preferred substituents on an carbocyclyl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro, cyano and oxo. Examples of preferred substituents on an carbocyclyl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano. Particularly preferred substituents include fluorine, chlorine, bromine, $C_{1-4}$ alkyl, $C_{1-4}$ alkoxy, $C_{1-4}$ haloalkyl, nitro and oxo. Examples of particularly preferred substituents include fluorine, chlorine, bromine, $C_{1-4}$ alkyl, $C_{1-4}$ alkoxy, $C_{1-4}$ haloalkyl and nitro. Further examples of particularly preferred substituents include fluorine, $C_{1-4}$ alkyl, $C_{1-4}$ alkoxy, $C_{1-4}$ haloalkyl and nitro.

As used herein, a heterocyclyl group is a non-aromatic saturated or unsaturated carbocyclic ring typically having from 5 to 10 carbon atoms, in which one or more, for example 1, 2 or 3, of the carbon atoms is replaced by a heteroatom selected from N, O and S. Saturated heterocyclyl groups are preferred. Examples include tetrahydrofuranyl, tetrahydrothienyl, pyrrolidinyl, imidazolidinyl, pyrazolidinyl, dioxolanyl, thiazolidinyl, tetrahydropyranyl, piperidinyl, dioxanyl, piperazinyl, morpholinyl, thiomorpholinyl and thioxanyl. Further examples include dithiolanyl, oxazolidinyl, tetrahydrothiopyranyl and dithianyl. Piperazinyl, piperidinyl and morpholinyl are preferred.

As used herein, references to a heterocyclyl group include fused ring systems in which a heterocyclyl group is fused to a phenyl group. Preferred such fused ring systems are those wherein a 5- to 6-membered heterocyclyl group is fused to a phenyl group. An example of such a fused ring system is a group wherein a 1H-imidazol-2(3H)-onyl group or a imidazolidin-2-onyl group is fused to a phenyl ring to form a 1H-benzo[d]imidazol-2(3H)-onyl group. Most preferably, however, a heterocyclyl group is monocyclic.

A heterocyclic group may be unsubstituted or substituted at any position. Typically, it carries 0, 1 or 2 substituents.

Suitable substituents on a heterocyclyl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbomyl, amino, mono($C_{1-6}$ alkyl)amino, di($C_{1-6}$ alkyl)amino, oxo, —$CO_2R'$, —$CONR'R''$, —$S(O)R'$, —$S(O)_2R'$, —$S(O)NR'R''$, —$S(O)_2NR'R''$, —NH—$S(O)_2R'$ or —NH—CO—R', wherein each R' and R" is the same or different and represents hydrogen or $C_{1-6}$ alkyl. Examples of suitable substituents on a heterocyclyl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbomyl, amino, mono($C_{1-6}$ alkyl)amino, di($C_{1-6}$ alkyl)amino, —$CO_2R'$, —$CONR'R''$, —$S(O)R'$, —$S(O)_2R'$, —$S(O)NR'R''$, —NH—$S(O)_2R'$ or —NH—CO—R', wherein each R' and R" is the same or different and represents hydrogen or $C_{1-6}$ alkyl.

Preferred substituents on a heterocyclyl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro, cyano and oxo. Examples of preferred substituents on a heterocyclyl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano. Particularly preferred substituents include fluorine, chlorine, bromine, $C_{1-4}$ alkyl, $C_{1-4}$ alkoxy, $C_{1-4}$ haloalkyl, nitro and oxo. Examples of particularly preferred substituents include fluorine, chlorine, bromine, $C_{1-4}$ alkyl, $C_{1-4}$ alkoxy, $C_{1-4}$ haloalkyl and nitro. Further examples of particularly preferred substituents include fluorine, $C_{1-4}$ alkyl, $C_{1-4}$ alkoxy, $C_{1-4}$ haloalkyl and nitro. Most preferably, a heterocyclyl group is unsubstituted or substituted by one or two $C_{1-2}$ alkyl groups.

As used herein, a halogen is typically chlorine, fluorine, bromine or iodine. It is preferably chlorine, fluorine or bromine. It is more preferably chlorine or fluorine.

As used herein, an alkoxy group is typically a said alkyl group attached to an oxygen atom. An alkylthio group is typically a said alkyl group attached to a thio group. A haloalkyl or haloalkoxy group is typically a said alkyl or alkoxy group substituted by one or more said halogen atoms. Typically, it is substituted by 1, 2 or 3 said halogen atoms. Preferred haloalkyl and haloalkoxy groups include perhaloalkyl and perhaloalkoxy groups such as —$CX_3$ and —$OCX_3$ wherein X is a said halogen atom, for example chlorine or fluorine. Particularly preferred haloalkyl groups are —$CF_3$ and —$CCl_3$. Particularly preferred haloalkoxy groups are —$OCF_3$ and —$OCCl_3$.

As used herein, a heteroaryl group is typically a 5- to 10 membered aromatic ring, such as a 5- or 6-membered ring, containing at least one heteroatom, for example 1, 2 or 3 heteroatoms, selected from O, S and N. Examples include pyridyl, pyrazinyl, pyrimidinyl, pyridazinyl, furanyl, thienyl, pyrazolidinyl, pyrrolyl, oxadiazolyl, isoxazolyl, thiadiazolyl, thiazolyl, imidazolyl and pyrazolyl groups. Further examples include oxazolyl and isothiazolyl. Preferred heteroaryl groups are pyridyl, thienyl, oxazolyl, isoxazolyl, furanyl and pyrazolyl. Examples of preferred heteroaryl groups are pyridyl, thienyl, isoxazolyl and furanyl. As used herein, references to a heteroaryl groups include fused ring systems in which a heteroaryl group is fused to a phenyl group. Preferred such fused ring systems are those wherein a 5- to 6-membered heteroaryl group is fused to a phenyl group. Examples of such fused ring systems are benzofuranyl, benzothiophenyl, indolyl, benzimidazolyl, benzoxazolyl, quinolinyl, quinazolinyl and isoquinolinyl moieties. Most preferably, however, a heterocyclyl group is monocyclic.

A heteroaryl group may be unsubstituted or substituted at any position. Typically, it carries 0, 1, 2 or 3 substituents.

Suitable substituents on a heteroaryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —$CONR'R''$, —$S(O)R'$, —$S(O)_2R'$, —$S(O)NR'R''$, —$S(O)_2NR'R''$, —NH—$S(O)_2R'$ or —NH—CO—R', wherein each R' and R'' is the same or different and represents hydrogen or $C_{1-6}$ alkyl. Examples of suitable substituents on a heteroaryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —$CONR'R''$, —$S(O)R'$, —$S(O)_2R'$, —$S(O)NR'R''$, —NH—$S(O)_2R'$ or —NH—CO—R', wherein each R' and R'' is the same or different and represents hydrogen or $C_{1-6}$ alkyl.

Preferred substituents on a heteroaryl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano. Particularly preferred substituents include fluorine, chlorine, bromine, $C_{1-4}$ alkyl, $C_{1-4}$ alkoxy, $C_{1-4}$ haloalkyl and nitro. Further preferred substituents include fluorine, chlorine, bromine, $C_{1-2}$ alkyl, $C_{1-2}$ haloalkyl and di($C_{1-2}$ alkyl)amino.

As used herein, references to a heteroaryl group include fused ring systems in which a heteroaryl group is fused to a monocyclic said aryl, carbocyclyl or heterocyclyl group, or to a further heteroaryl group. Preferred such ring systems are those wherein a heteroaryl group is fused to an aryl group, for example a phenyl group. An example of such a fused ring system is a group wherein a thienyl group is fused to a phenyl ring to form a benzothienyl group. A further example of such a fused ring system is a group wherein a furanyl group is fused to a phenyl ring to form a benzofuranyl group.

When $R^1$ is an aryl or heteroaryl group it is typically unsubstituted or substituted by one, two or three substituents selected from halogen, $C_{1-6}$ alkyl, $C_{1-6}$ alkoxy, $C_{1-6}$ alkylthio, $C_{1-6}$ haloalkyl or $C_{1-6}$ haloalkoxy. Preferably, it is unsubstituted or substituted by one or two substituents selected from fluorine, chlorine, bromine, $C_{1-4}$ alkyl, $C_{1-4}$ alkoxy, $C_{1-4}$ alkylthio, $C_{1-4}$ haloalkyl or $C_{1-4}$ haloalkoxy. More preferably, it is unsubstituted or substituted by a single fluorine, chlorine, $C_{1-2}$ alkyl, $C_{1-2}$ alkoxy, $C_{1-2}$ alkylthio, $C_{1-2}$ haloalkyl or $C_{1-2}$ haloalkoxy substituent.

Typically, $R^1$ is $C_{1-6}$ alkyl or aryl. Preferably, $R^1$ is $C_{1-2}$ alkyl or aryl. More preferably, $R^1$ is $C_{1-2}$ alkyl or phenyl. More preferably, $R^1$ is phenyl.

Typically, $R^2$ is hydrogen or $C_{1-4}$ alkyl. Preferably, $R^2$ is hydrogen.

Typically, $R^3$ is halogen, hydroxy, $C_{1-4}$ alkyl, $C_{1-4}$ alkoxy, $C_{1-4}$ alkylthio, $C_{1-4}$ haloalkyl, $C_{1-4}$ haloalkoxy, amino, mono($C_{1-4}$ alkyl)amino or di($C_{1-4}$ alkyl)amino. Preferably, $R^3$ is fluorine, chlorine, bromine, $C_{1-2}$ alkyl, $C_{1-2}$ alkoxy, $C_{1-2}$ alkylthio, $C_{1-2}$ haloalkyl, $C_{1-2}$ haloalkoxy, amino, mono($C_{1-2}$ alkyl)amino or di($C_{1-2}$ alkyl)amino. More preferably, $R^3$ is methyl, trifluoromethyl, fluorine, chlorine or bromine. Most preferably, $R^3$ is methyl or chlorine. An example of a most preferred group is when $R^3$ is chlorine.

Typically, n is 0, 1 or 2. Preferably, n is 0 or 1.

Typically, $R^4$ is hydrogen or $C_{1-4}$ alkyl. Preferably, $R^4$ is hydrogen or $C_{1-2}$ alkyl. More preferably, $R^4$ is hydrogen or methyl. Most preferably, $R^4$ is hydrogen.

When $R^5$ is a heterocyclyl group, it is typically attached via a carbon atom. Typically, $R^5$ is $C_{1-6}$ alkyl, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)-, aryl-C(O)—C(O)—, heteroaryl-C(O)—C(O)— or —$XR^6$. Examples of typical $R^5$ groups are those wherein $R^5$ is $C_{1-6}$ alkyl, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)- or —$XR^6$.

Preferably, $R^5$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example piperidinyl, morpholinyl and piperazinyl, phenyl-($C_{1-2}$ alkyl)-, for example benzyl, heteroaryl-($C_{1-2}$ alkyl)-, phenyl-C(O)—C(O)—, heteroaryl-C(O)—C(O)— or —$XR^6$. Examples of preferred $R^5$ groups are those wherein $R^5$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example piperidinyl, morpholinyl and piperazinyl, phenyl-($C_{1-2}$ alkyl)-, for example benzyl, heteroaryl-($C_{1-2}$ alkyl)- or —$XR^6$.

More preferably, $R^5$ is $C_{1-4}$ alkyl, phenyl, thienyl, furanyl, isoxazolyl, pyridyl, cyclopentyl, cyclohexyl, benzothienyl, dihydrobenzofuranyl, phenyl-$CH_2$—, furanyl-$CH_2$—, phenyl-C(O)—C(O)—, thienyl-C(O)—C(O)— or —$XR^6$. Examples of more preferred $R^5$ groups are those wherein $R^5$ is $C_{1-4}$ alkyl, phenyl, thienyl, furanyl, isoxazolyl, pyridyl, cyclopentyl, cyclohexyl, benzothienyl, dihydrobenzofuranyl, phenyl-$CH_2$—, furanyl-$CH_2$— or —$XR^6$.

Most preferably, $R^5$ is phenyl-$CH_2$—, furanyl-$CH_2$—, —C(O)—C(O)-thienyl or —$XR^6$. Examples of most preferred $R^5$ groups are those wherein $R^5$ is phenyl-$CH_2$—, furanyl-$CH_2$— or —$XR^6$.

Typically, X is —CO—, —S(O)— or —$S(O)_2$—. Preferably, X is —CO— or —$S(O)_2$—.

When $R^6$ is a group —NR'R'' and either R' or R'' includes an aryl, heteroaryl, carbocyclyl or heterocyclyl moiety it is typically unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, nitro and cyano. Preferably, the aryl, heteroaryl, carbocyclyl or heterocyclyl moiety is unsubstituted or substituted by 1 or 2 substituents selected from fluorine, chlorine, bromine, $C_{1-4}$ alkyl, $C_{1-4}$ alkoxy, $C_{1-4}$ alkylthio, $C_{1-4}$ haloalkyl, $C_{1-4}$ haloalkoxy and nitro. An example of preferred substitution is when the aryl, heteroaryl, carbocyclyl or heterocyclyl moiety is unsubstituted or substituted by 1 or 2 substituents selected from fluorine, chlorine, bromine, $C_{1-4}$ alkyl, $C_{1-4}$ alkoxy, $C_{1-4}$ haloalkyl and nitro. More preferably, the aryl, heteroaryl, carbocyclyl or heterocyclyl moiety is unsubstituted or substituted by one or two substituents selected from fluorine, chlorine, bromine, $C_{1-2}$ alkyl, $C_{1-2}$ alkoxy, $C_{1-2}$ alkylthio, $C_{1-2}$ haloalkyl and nitro. An example of more preferred substitution is when the aryl, heteroaryl, carbocyclyl or heterocyclyl moiety is unsubstituted or substituted by a single fluoro, chloro, methyl, methoxy or nitro substituent. When R' or R'' is a heteroaryl or heterocyclyl group, it is attached via a carbon atom.

Typically, R' and R'' in the group —NR'R'' are not both hydrogen. Typically, each R' and R'' is the same or different and represents hydrogen, $C_{1-4}$ alkyl, aryl, heteroaryl, carbocyclyl, aryl-($C_{1-4}$ alkyl)- or heteroaryl-($C_{1-4}$alkyl)-. Examples of typical R' and R'' groups are those wherein each R' and R" is the same or different and represents hydrogen, $C_{1-4}$ alkyl, phenyl, heteroaryl, for example thienyl, carbocyclyl, for example cyclohexyl or cyclopentyl, or phenyl-($C_{1-4}$ alkyl)-. Further examples of typical R' and R" groups are those wherein each R' and R" is the same or different and represents hydrogen, $C_{1-4}$ alkyl, phenyl, thienyl, cyclohexyl, cyclopentyl or phenyl-($CH_2$)—. Preferably, each R' and R" is the same or different and represents hydrogen, $C_{1-4}$ alkyl, phenyl, phenyl-$CH_2$—, cyclohexyl or cyclopentyl. More preferably, one of R' and R" represents hydrogen. Most preferably, one of R' and R" is hydrogen and the other is $C_{1-4}$ alkyl, phenyl, phenyl-$CH_2$—, cyclohexyl or cyclopentyl. As an additional preference, one of R' and R" is hydrogen and the other is $C_{1-4}$ alkyl, phenyl, thienyl or phenyl-$CH_2$—.

Typically, $R^6$ is $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)-, aryl-($C_{1-4}$ hydroxyalkyl)-, heteroaryl-($C_{1-4}$ hydroxyalkyl)-, carbocyclyl-($C_{1-4}$ hydroxyalkyl)-, heterocyclyl-($C_{1-4}$ hydroxyalkyl)-, aryl-($C_{1-4}$ alkyl)-O—, heteroaryl-($C_{1-4}$ alkyl)-O—, carbocyclyl-($C_{1-4}$ alkyl)-O—, heterocyclyl-($C_{1-4}$ alkyl)-O— or —NR'R" wherein R' and R" are as defined above. Examples of typical $R^6$ groups are those wherein $R^6$ is $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)- or —NR'R" wherein R' and R" are as defined above.

Preferably, $R^6$ is $C_{1-6}$ alkyl, $C_{1-6}$ alkoxy, $C_{1-6}$ alkylthio, aryl, for example phenyl, naphthyl, dihydrobenzofuranyl, benzodioxinyl, 9H-fluoren-9-onyl and indolyl, heteroaryl, for example thienyl, furanyl, oxazolyl, isoxazolyl, pyrazolyl, pyridyl, benzothienyl and benzofuranyl, carbocyclyl, for example cyclopentyl and cyclohexyl, heterocyclyl, for example piperazinyl, piperidinyl, morpholinyl and 1H-benzo[d]imidazol-2(3H)-onyl, phenyl-($C_{1-2}$ alkyl)-, phenyl-($C_{1-2}$ alkyl)-O—, phenyl-($C_{1-2}$ hydroxyalkyl)-, heteroaryl-($C_{1-2}$ hydroxyalkyl)-, heteroaryl-($C_{1-2}$ alkyl)- or —NR'R" wherein R' and R" are as defined above. Examples of preferred $R^6$ groups are those wherein $R^6$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example N-heterocyclyl, phenyl-($C_{1-2}$ alkyl)-, for example benzyl, heteroaryl-($C_{1-2}$ alkyl)- or —NR'R" wherein R' and R" are as defined above.

More preferably, $R^6$ is $C_{1-4}$ alkyl, $C_{1-4}$ alkoxy, phenyl, naphthyl, dihydrobenzofuranyl, benzodioxinyl, 9H-fluoren-9-onyl, indolyl, thienyl, furanyl, oxazolyl, isoxazolyl, pyrazolyl, pyridyl, benzothienyl, benzofuranyl, cyclopentyl, cyclohexyl, piperazinyl, piperidinyl, morpholinyl, phenyl-($C_{1-2}$ alkyl)-, phenyl-$CH_2$—CH(OH)—, phenyl-CH(OH)—$CH_2$—, phenyl-($C_{1-2}$ alkyl)-O—, 1H-benzo[d]imidazol-2(3H)-onyl or —NR'R" wherein R' and R" are as defined above. Example of most preferred $R^6$ groups are those wherein $R^6$ is $C_{1-4}$ alkyl, phenyl, thienyl, furanyl, pyridyl, cyclopentyl, cyclohexyl, benzothienyl, dihydrobenzofuranyl, isoxazolyl, piperidinyl, for example N-piperidinyl, morpholinyl, for example N-morpholinyl, piperazinyl, for example N-piperazinyl, or —NR'R" wherein R' and R" are as defined above.

Preferred compounds of the formula (I) are those in which:
$R^1$ is $C_{1-6}$ alkyl or aryl;
$R^2$ is hydrogen or $C_{1-4}$ alkyl;
$R^3$ is halogen, hydroxy, $C_{1-4}$ alkyl, $C_{1-4}$ alkoxy, $C_{1-4}$ alkylthio, $C_{1-4}$ haloalkyl, $C_{1-4}$ haloalkoxy, amino, mono($C_{1-4}$ alkyl)amino or di($C_{1-4}$ alkyl)amino or, preferably, $R^3$ is fluorine, chlorine, bromine, $C_{1-2}$ alkyl, $C_{1-2}$ alkoxy, $C_{1-2}$ alkylthio, $C_{1-2}$ haloalkyl, $C_{1-2}$ haloalkoxy, amino, mono ($C_{1-2}$ alkyl)amino or di ($C_{1-2}$ alkyl)amino;
n is 0, 1 or 2;
$R^4$ is hydrogen or $C_{1-4}$ alkyl;
$R^5$ is $C_{1-6}$ alkyl, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)-, aryl-C(O)—C(O)—, heteroaryl-C(O)—C(O)— or $XR^6$;
X is —CO—, —S(O)— or —S(O)$_2$—; and
$R^6$ is $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)-, aryl-($C_{1-4}$ hydroxyalkyl)-, heteroaryl-($C_{1-4}$ hydroxyalkyl)-, carbocyclyl-($C_{1-4}$ hydroxyalkyl)-, heterocyclyl-($C_{1-4}$ hydroxyalkyl)-, aryl-($C_{1-4}$ alkyl)-O—, heteroaryl-($C_{1-4}$ alkyl)-O—, carbocyclyl-($C_{1-4}$ alkyl)-O—, heterocyclyl-($C_{1-4}$ alkyl)-O— or —NR'R", wherein each R' and R" is the same or different and represents hydrogen, $C_{1-4}$ alkyl, aryl, heteroaryl, carbocyclyl, aryl-($C_{1-4}$ alkyl)- or heteroaryl-($C_{1-4}$ alkyl)-, the aryl moiety in the $R^1$ group being unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl or $C_{1-6}$ haloalkoxy;

the aryl and heteroaryl moieties in the groups $R^5$ and $R^6$ being unsubstituted or substituted by 1, 2 or 3 substituents selected from halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbomyl, amino, mono($C_{1-6}$ alkyl)amino, di($C_{1-6}$ alkyl)amino, —CO$_2$R', —CONR'R", —S(O)R', —S(O)$_2$R', —S(O)NR'R", —S(O)$_2$NR'R", —NH—S(O)$_2$R' or —NH—CO—R', wherein each R' and R" is the same or different and represents hydrogen or $C_{1-6}$ alkyl;

the carbocyclyl and heterocyclyl moieties in the groups $R^5$ and $R^6$ being unsubstituted or substituted by 1, 2 or 3 substituents selected from halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbomyl, amino, mono($C_{1-6}$ alkyl)amino, di($C_{1-6}$ alkyl)amino, oxo, —CO$_2$R', —CONR'R", —S(O)R', —S(O)$_2$R', —S(O)NR'R", —S(O)$_2$NR'R", —NH—S(O)$_2$R' or —NH—CO—R', wherein each R' and R" is the same or different and represents hydrogen or $C_{1-6}$ alkyl; and the alkyl moieties in the aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)- groups of $R^6$ being unsubstituted or substituted by one or two hydroxy substituents.

Preferably, in these preferred compounds of formula (I), the aryl, heteroaryl and carbocyclyl moieties in the groups R' and R" are unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, nitro and cyano.

Further preferred compounds of formula (I) are those wherein:
$R^1$ is $C_{1-2}$ alkyl or phenyl;
$R^2$ is hydrogen or $C_{1-4}$ alkyl;
$R^3$ is methyl, trifluoromethyl, fluorine, chlorine or bromine;
n is 0 or 1;
$R^4$ is hydrogen or $C_{1-2}$ alkyl;
$R^5$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example piperidinyl, morpholinyl and piperazinyl, phenyl-($C_{1-2}$ alkyl)-, for example benzyl, heteroaryl-($C_{1-2}$ alkyl)-, phenyl-C(O)—C(O)—, heteroaryl-C(O)—C(O)— or —$XR^6$, provided that when $R^5$ is heterocyclyl it is attached via a carbon atom;

X is —CO—, —S(O)— or —$S(O)_2$—; and $R^6$ is $C_{1-6}$ alkyl, $C_{1-6}$ alkoxy, $C_{1-6}$ alkylthio, aryl, for example phenyl, naphthyl, dihydrobenzofuranyl, benzodioxinyl, 9H-fluoren-9-onyl and indolyl, heteroaryl, for example thienyl, furanyl, oxazolyl, isoxazolyl, pyrazolyl, pyridyl, benzothienyl and benzofuranyl, carbocyclyl, for example cyclopentyl and cyclohexyl, heterocyclyl, for example piperazinyl, piperidinyl, morpholinyl and 1H-benzo[d]imidazol-2(3H)-onyl, phenyl-($C_{1-2}$ alkyl)-, phenyl-($C_{1-2}$ alkyl)-O—, phenyl-($C_{1-2}$ hydroxyalkyl)-, heteroaryl-($C_{1-2}$ hydroxyalkyl)-, heteroaryl-($C_{1-2}$ alkyl)- or —NR'R" wherein each R' and R" is the same or different and represents hydrogen, $C_{1-4}$ alkyl, phenyl, heteroaryl, for example thienyl, carbocyclyl, for example cyclohexyl or cyclopentyl, or phenyl-($C_{1-4}$ alkyl)-, the phenyl moiety in the $R^1$ group being unsubstituted or substituted by one or two substituents selected from fluorine, chlorine, bromine, $C_{1-4}$ alkyl, $C_{1-4}$ alkoxy, $C_{1-4}$ alkylthio, $C_{1-4}$ haloalkyl or $C_{1-4}$ haloalkoxy;

the aryl moieties in the groups $R^5$ and $R^6$ being unsubstituted or substituted by 1, 2 or 3 substituents selected from halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, amino, mono($C_{1-6}$ alkyl)amino, di($C_{1-6}$ alkyl)amino, nitro, cyano, —$CO_2R'$, —S(O)R', —$S(O)_2R'$ and —$S(O)_2NR'R''$, wherein each R' and R" is the same or different and represents hydrogen or $C_{1-4}$ alkyl;

the heteroaryl moieties in the groups $R^5$ and $R^6$ being unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano; and the carbocyclyl and heterocyclyl moieties in the groups $R^5$ and $R^6$ being unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro, cyano and oxo; and the alkyl moiety in the phenyl-($C_{1-2}$ alkyl)- and heteroaryl-($C_{1-2}$ alkyl)- groups of $R^6$ being unsubstituted or substituted by a single hydroxy substituent.

Preferably, in these further preferred compounds of formula (I), the phenyl, heteroaryl and carbocyclyl moieties in the groups R' and R" are unsubstituted or substituted by 1 or 2 substituents selected from fluorine, chlorine, bromine, $C_{1-4}$ alkyl, $C_{1-4}$ alkoxy, $C_{1-4}$ alkylthio, $C_{1-4}$ haloalkyl, $C_{1-4}$ haloalkoxy and nitro.

Particularly preferred compounds of formula (I) are compounds of formula (Ia) and pharmaceutically acceptable salts thereof

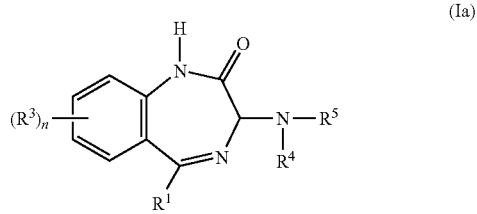

(Ia)

wherein:

$R^1$ is phenyl or methyl;

$R^3$ is methyl or chlorine;

n is 0 or 1;

$R^4$ is hydrogen or methyl;

$R^5$ is phenyl-$CH_2$—, furanyl-$CH_2$—, thienyl-C(O)—C(O)— or $XR^6$;

X is —CO— or —$S(O)_2$—; and $R^6$ is $C_{1-4}$ alkyl, $C_{1-4}$ alkoxy, phenyl, naphthyl, dihydrobenzofuranyl, benzodioxinyl, 9H-fluoren-9-onyl, indolyl, thienyl, furanyl, oxazolyl, isoxazolyl, pyrazolyl, pyridyl, benzothienyl, benzofuranyl, cyclopentyl, cyclohexyl, piperazinyl, piperidinyl, morpholinyl, phenyl-($C_{1-2}$ alkyl)-, phenyl-$CH_2$—CH(OH)—, phenyl-CH(OH)—$CH_2$—, phenyl-($C_{1-2}$ alkyl)-O—, 1H-benzo[d]imidazol-2(3H)-onyl or —NR'R" wherein each R' and R" is the same or different and represents hydrogen, $C_{1-4}$ alkyl, phenyl, thienyl, cyclohexyl, cyclopentyl or phenyl-($CH_2$)—, the phenyl moiety in the group $R^1$ being unsubstituted or substituted by a single fluorine, chlorine, $C_{1-2}$ alkyl, $C_{1-2}$ alkoxy, $C_{1-2}$ alkylthio, $C_{1-2}$ haloalkyl or $C_{1-2}$ haloalkoxy substituent;

the aryl moieties in the groups $R^5$ and $R^6$ being unsubstituted or substituted by 1, 2 or 3 substituents selected from fluorine, chlorine, bromine, iodine, $C_{1-4}$ alkyl, $C_{2-4}$ acyl, hydroxy, $C_{1-4}$ alkoxy, $C_{1-4}$ alkylthio, $C_{1-4}$ haloalkyl, $C_{1-4}$ haloalkoxy, amino, mono($C_{1-4}$ alkyl)amino, di($C_{1-4}$ alkyl)amino, nitro, —$CO_2R'$, —$S(O)_2R'$ and —$S(O)_2NH_2$, wherein R' represents $C_{1-2}$ alkyl;

the heteroaryl moieties in the groups $R^5$ and $R^6$ being unsubstituted or substituted by 1 or 2 substituents selected from fluorine, chlorine, bromine, $C_{1-2}$ alkyl, $C_{1-2}$ haloalkyl and di($C_{1-2}$ alkyl)amino; and the heterocyclyl and carbocyclyl moieties in the $R^6$ group being unsubstituted or substituted by 1 or 2 substituents selected from fluorine, chlorine, bromine, $C_{1-4}$ alkyl, $C_{1-4}$ alkoxy, $C_{1-4}$ haloalkyl and nitro.

Preferably, in the compounds of formula (Ia), $R^1$ is phenyl. Preferably, $R^3$ is chlorine. Preferably, $R^5$ is —CO—$R^6$. Preferably, $R^6$ is phenyl, 5- to 6-membered heteroaryl (for example furanyl) or —NH-phenyl. Preferably, $R^1$ is unsubstituted or substituted by a halogen or $C_1$-$C_2$ haloalkyl substitutent. Preferably, the phenyl and heteroaryl moieties in $R^6$ are unsubstituted or substituted by 1 or 2 $C_1$-$C_2$ alkyl, $C_1$-$C_2$ alkoxy, halogen, $C_1$-$C_2$ haloalkyl, $C_1$-$C_2$ haloalkoxy or nitro substituents. More preferably, the heteroaryl moieties in $R^6$ are unsubstituted.

Further preferred compounds of the invention are compounds of formula (Ib)

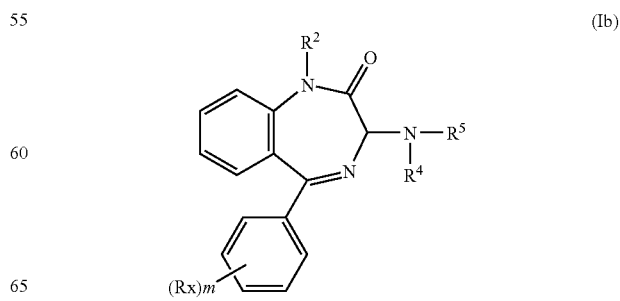

(Ib)

wherein:
R² is hydrogen or C₁-C₄ alkyl;
R⁴ is hydrogen or methyl;
R⁵ is phenyl, —CO—CO-phenyl, —CO—CO— (5- to 6-membered heteroaryl) or —X—R⁶;
X is —CO—;
R⁶ is C₁-C₄ alkyl, phenyl or 5- to 6-membered heteroaryl;
m is 0 or 1; and
each Rx is the same or different and represents fluorine, chlorine, C₁-C₂ alkyl, C₁-C₂ alkoxy, C₁-C₂ haloalkyl or C₁-C₂ haloalkoxy,
the phenyl moiety in the group R⁶ being unsubstituted or substituted by 1, 2 or 3 substituents selected from halogen, C₁-C₄ alkyl, C₂-C₄ acyl, C₁-C₄ alkoxy, hydroxy, C₁-C₄ haloalkyl and C₁-C₄ haloalkoxy substituents; and
the heteroaryl moieties in the group R⁶ being unsubstituted or substituted by 1 or 2 substituents selected from halogen, C₁-C₂ alkyl, C₁-C₂ alkoxy, C₁-C₂ haloalkyl and C₁-C₂ haloalkoxy substituents.

Preferably, in the formula (Ib), R² is hydrogen.
Preferably, in the formula (Ib), R⁴ is hydrogen.
Preferably, in the formula (Ib), R⁵ is —CO—R⁶.
Preferably, in the formula (Ib), R⁶ is a phenyl or 5- to 6-membered heteroaryl group (for example thienyl) which is unsubstituted or substituted by 1 or 2 C₁-C₂ alkyl, C₁-C₂ alkoxy, halogen, C₁-C₂ haloalkyl or C₁-C₂ haloalkoxy substituents. More preferably, R⁶ is a phenyl group which is unsubstituted or substituted by 1 or 2 C₁-C₂ alkyl, C₁-C₂ alkoxy or halogen substituents, or is a thienyl group which is unsubstituted or substituted by 1 or 2 halogen atoms.
Preferably, in the formula (Ib), m is 1.
Preferably, in the formula (Ib), Rx is present at the para position.
Preferably, in the formula (Ib), Rx is halogen, more preferably chlorine.

Most preferred compounds of the invention are compounds of formula (Ib')

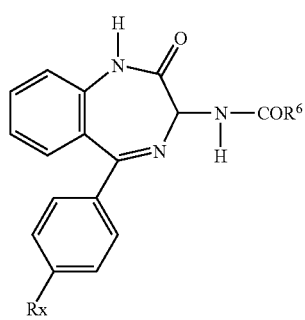

wherein:
Rx is halogen, preferably chlorine; and
R⁶ is a phenyl or 5- to 6-membered heteroaryl group (for example thienyl) which is unsubstituted or substituted by 1 or 2 C₁-C₂ alkyl, C₁-C₂ alkoxy, halogen, C₁-C₂ haloalkyl or C₁-C₂ haloalkoxy substituents.

Compounds of the formula (I) containing one or more chiral centre may be used in enantiomerically or diastereoisomerically pure form, or in the form of a mixture of isomers. For the avoidance of doubt, the chemical structures depicted herein are intended to embrace all stereoisomers of the compounds shown, including racemic and non-racemic mixtures and pure enantiomers and/or diastereoisomers.

Preferred compounds of the formula (I) are optically active isomers. Thus, for example, preferred compounds of formula (I) containing only one chiral centre include an R enantiomer in substantially pure form, an S enantiomer in substantially pure form and enantiomeric mixtures which contain an excess of the R enantiomer or an excess of the S enantiomer. For the avoidance of doubt, the compounds of the formula (I) can, if desired, be used in the form of solvates.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutical acceptable bases include alkali metal (e.g. sodium or potassium) and alkaline earth metal (e.g. calcium or magnesium) hydroxides and organic bases such as alkyl amines, aralkyl amines or heterocyclic amines.

Preferred compounds of formula (I) are:
N-[5-(4-Chloro-phenyl)-2-oxo-2,3-dihydro-1H-benzo[e][1,4]diazepin-3-yl]-2-ethoxy benzamide;
(S)—N-[5-(4-Chloro-phenyl)-2-oxo-2,3-dihydro-1H-benzo[e][1,4]diazepin-3-yl]-2-ethoxy-benzamide;
N-[5-(4-Chloro-phenyl)-2-oxo-2,3-dihydro-1H-benzo[e][1,4]diazepin-3-yl]-2,5-dimethoxy-benzamide;
(S)—N-[5-(4-Chloro-phenyl)-2-oxo-2,3-dihydro-1H-benzo[e][1,4]diazepin-3-yl]-2,5-dimethoxy-benzamide;
(R)—N-[5-(4-Chloro-phenyl)-2-oxo-2,3-dihydro-1H-benzo[e][1,4]diazepin-3-yl]-2,5-dimethoxy-benzamide;
N-[5-(4-Chloro-phenyl)-2-oxo-2,3-dihydro-1H-benzo[e][1,4]diazepin-3-yl]-5-fluoro-2-methoxy-benzamide;
(S)—N-[5-(4-Chloro-phenyl)-2-oxo-2,3-dihydro-1H-benzo[e][1,4]diazepin-3-yl]-5-fluoro-2-methoxy-benzamide;
(R)—N-[5-(4-Chloro-phenyl)-2-oxo-2,3-dihydro-1H-benzo[e][1,4]diazepin-3-yl]-5-fluoro-2-methoxy-benzamide;
5-Chloro-N-[5-(4-chloro-phenyl)-2-oxo-2,3-dihydro-1H-benzo[e][1,4]-diazepin-3-yl]-2-methoxy-benzamide;
(S)-5-Chloro-N-[5-(4-chloro-phenyl)-2-oxo-2,3-dihydro-1H-benzo[e][1,4]-diazepin-3-yl]-2-methoxy-benzamide;
(R)—N-[5-(4-Chloro-phenyl)-2-oxo-2,3-dihydro-1H-benzo[e][1,4]diazepin-3-yl]-5-fluoro-2-methoxy-benzamide;
3-Bromo-thiophene-2-carboxylic acid [5-(4-chloro-phenyl)-2-oxo-2,3-dihydro-1H-benzo[e][1,4]diazepin-3-yl]-amide;
(S)-3-Bromo-thiophene-2-carboxylic acid [5-(4-chloro-phenyl)-2-oxo-2,3-dihydro-1H-benzo[e][1,4]diazepin-3-yl]-amide;
and pharmaceutically acceptable salts thereof.

Further, the disclosure of WO 04/026843 is incorporated herein by reference. Any of the compounds disclosed in that document as RSV inhibitors can be used in the treatment or prevention of an HCV infection in accordance with the present invention.

Compounds of formula (I) may be prepared by reacting glyoxylic acid (HCO—CO₂H), benzotriazole and an appropriate benzyl carbamate at reflux in toluene, under Dean-Stark conditions giving the key protected amino acid of formula (II')

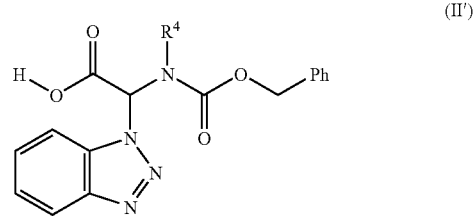

The thus obtained amino acid of formula (II') can then be reacted with a suitable chlorinating agent, such as oxalyl chloride, followed by reaction with a 2-aminobenzophenone of formula (III')

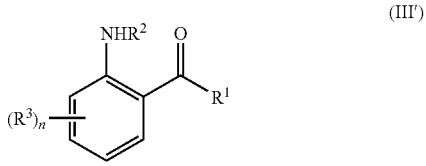

to give the intermediate amide of formula (IV')

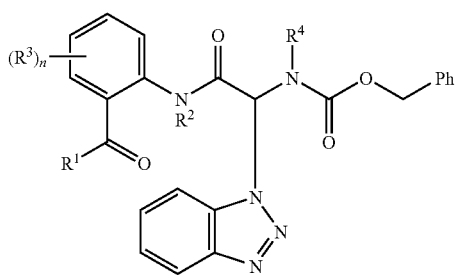

which need not be characterized.

The compound of formula (IV') can then be subjected to ammonolysis followed by ring closure in acetic acid containing ammonium acetate to obtain the protected benzodiazepine of formula (V')

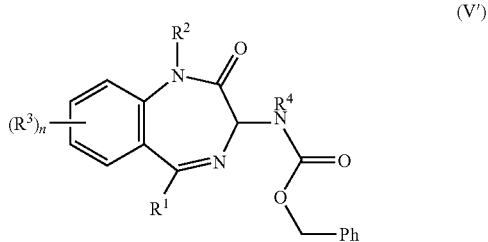

The compound of formula (V') can then be deprotected using hydrogen bromide in acetic acid to yield the deprotected amine of formula (VI').

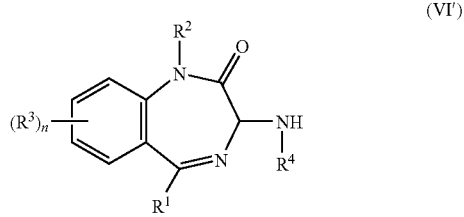

Compounds of formula (I), in which $R^5$ is $XR^6$ and X is —CO— can be prepared by reacting a compound of formula (VI'), as defined above, with an acid anhydride in a suitable solvent, preferably pyridine at ambient temperature, or with an acid chloride in a suitable solvent in the presence of a base, preferably in THF at ambient temperature with triethylamine present. Alternatively, the compounds can be produced by reaction of a compound of formula (VI') with an acid in a suitable solvent in the presence of a base and a coupling agent, preferably in THF at ambient temperature with triethylamine and O-benzotriazol-1-yl-N,N,N',N'-tetramethyluronium hexafluorophosphate (HBTU) present.

If the acid chloride used is an amino carbonyl chloride, the compound of formula (I) is a tertiary urea. In the case where $R^6$ is NH—R', such compounds may be prepared by the reaction of a compound of formula (VI') with an isocyanate. This reaction is preferably carried out in THF at ambient temperature. Alternatively, the isocyanate may be prepared in situ from the relevant amine and phosgene, in the presence of a base, usually triethylamine, again in THF.

Compounds of formula (I), in which $R^5$ is —$XR^6$ and X is —$S(O)_2$— may be prepared by the reaction of a compound of formula (VI') with a suitable sulfonyl chloride. Similarly, compounds of formula (I), in which $R^5$ is $XR^6$ and X is —S(O)— may be prepared by the reaction of a compound of formula (VI') with a suitable sulfinyl chloride.

Compounds of formula (I) in which $R^5$ is not $XR^6$ may be prepared by known methods. For example, a compound of formula (VI') can be reacted with a compound of formula $R^5$-L, wherein L is a leaving group such as a chlorine atom, a mesylate group or a triflate group. When $R^5$ is aryl or heteroaryl, L can be —$B(OH)_2$ and the reaction may take place in the presence of copper acetate. Such boronic acid coupling reactions will, of course, be familiar to those of skill in the art. Compounds wherein $R^5$ is aryl or heteroaryl may also be prepared by way of a Buchwald reaction or by reaction of a compound of formula (VI') with an appropriate fluoroaryl or fluoroheteroaryl compound. Compounds wherein $R^5$ is a heteroaryl group may also be prepared by reaction of a compound of formula (VI') with a suitable chloroheteroaryl or bromoheteroaryl compound. Compounds wherein $R^5$ is a carbocyclyl group may also be prepared by known methods, for example a compound wherein $R^5$ is cyclohexyl may be prepared by the reaction of a compound of formula (VI') with cyclohexanone in the presence of a reducing agent.

Compounds of formula (I) in which the $R^5$ group is aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)- can also be prepared by the reaction of a compound of formula (VI') with an aldehyde in the presence of a reducing agent. Preferably, such reactions between compounds of formula (VI') and aldehydes are carried out in a mixture of dichloromethane and acetic acid in the presence of sodium (triacetoxy)borohydride at ambient temperature.

In the preparation of the benzodiazepine skeleton, commercially available aminobenzophenone compounds of formula (III') can be used where possible. Compounds of formula (III') which are not commercially available can be prepared by known methods, for example by reaction of a Weinreb type amide of formula (VII')

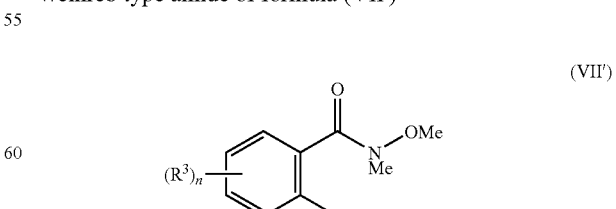

with a group $R^1$—Li or a Grignard reagent such as $R^1$—MgBr. Preferably this reaction is carried out in THF at –100° C.

Compounds of formula (VII') are known compounds or can be prepared by analogy with known methods. For example, they can be prepared from the reaction of isatoic anhydrides of formula (VIII')

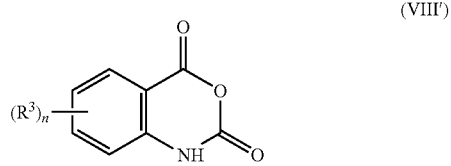

(VIII')

with N,O-dimethyl hydroxylamine under standard reaction conditions.

The starting materials of formula (II'), (III'), (VII'), and (VIII') are known compounds, or may be prepared by analogy with known methods.

Further synthetic manipulation of the thus obtained compounds of formula (I) may be carried out by conventional methods to achieve further compounds of formula (I). The benzodiazepines of formula (I) can be salified by treatment with an appropriate acid or base.

Although the described route to the claimed compounds provides an adequate synthesis for laboratory scale preparations, an alternative route was sought which has potential as a manufacturing route. The same starting material (2-aminobenzophenone) (1) is used in both, however in the alternative route, the benzodiazepine ring system is formed by reaction initially with bromoacetyl bromide (or an equivalent reagent) followed by ring closure with ammonia. These reactions are carried out in a suitable solvent, such as dichloromethane, and at a suitable temperature which may range from −20 to 150° C. In order to protect the NH functionality, at this stage the unsubstituted benzodiazepine is reacted with a base, and an alkylating agent. For instance sodium hydride in DMF followed by addition of 4-methoxy-benzyl chloride gives rise to the intermediate (2) shown below. Further reaction of this material with a base (e.g. potassium tert-butoxide) in a suitable solvent (e.g. THF or DMF) followed by quenching with isoamyl nitrite (or an alternative similar reagent) furnishes the oxime intermediate (3) which may be converted into the racemic primary amine by methods which include the use of hydrogen and a suitable catalyst. This amine then undergoes a Dynamic Kinetic Resolution (DKR) procedure by which the racemic amine in the presence of a suitable optically active acid, and a suitable aldehyde gives rise to precipitation of the salt of the desired (S)-amine (4) in good yield and exceptionally high enantiomeric excess. A suitable acid for this conversion can be e.g. Camphorsulfonic acid, Boc-phenyl alanine or the like, and a suitable aldehyde may be a benzaldehyde such as 3,5-dichloro salicylaldehyde.

The optically amine thus formed may then be transformed into a desired derivative, such as an amide or urea. The amide formations may be carried out using a suitable carboxylic acid and a coupling reagent, or a carbonyl chloride or other suitable reagent, and the ureas prepared using either a suitable isocyanate, or alternatively reaction with phosgene followed by a suitable amine.

These derivatives thus formed may then have the protecting group removed. This may be carried out in the presence of a Lewis Acid, such as aluminium chloride, boron trifluoride, titanium tetrachloride, or the like. These reactions are carried out in a suitable inert solvent, such as dichloromethane. Reaction temperatures may range from −20 to 150° C., but are typically carried out at room temperature or below.

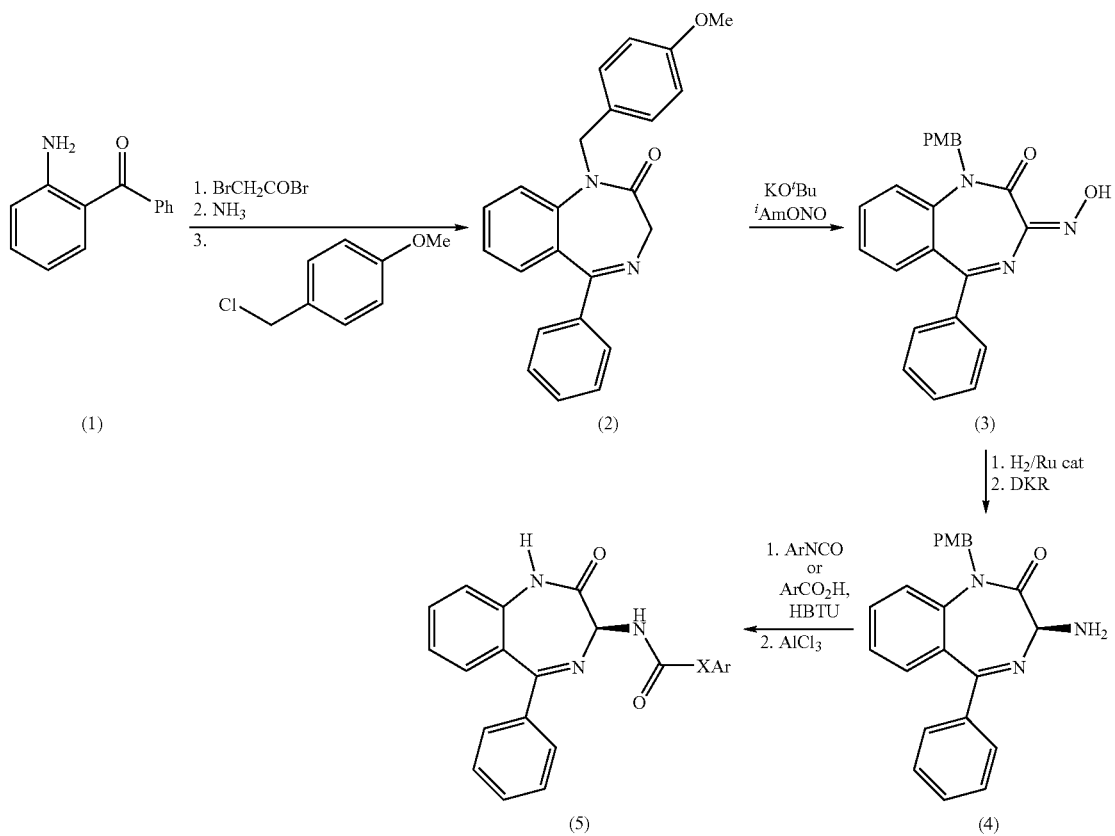

Further techniques for preparing the benzodiazepines of the formula (I) are given in WO 04/026843.

The present invention provides the use of a benzodiazepine derivative of formula (I), as defined above, or a pharmaceutically acceptable salt thereof, in the manufacture of a medicament for use in treating or preventing a hepatitis C infection.

Further, certain compounds of the invention are believed to be novel. The present invention therefore also provides the compounds of formula (Ib) and (Ib'), and pharmaceutically acceptable salts thereof, per se.

Typically, the above compounds are for use in the treatment of the human or animal body. The present invention also provides a pharmaceutical composition comprising a compound as defined above and a pharmaceutically acceptable carrier or diluent.

Also provided is a method of treating or preventing a hepatitis C infection in a patient, which method comprises administering to said patient a benzodiazepine derivative of formula (I), as defined above, or a pharmaceutically acceptable salt thereof.

The anti-HCV benzodiazepines of the formula (I) may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories. In a preferred embodiment, administration is by intravenous, intranasal or intrabronchial means.

The anti-HCV benzodiazepines of the formula (I) are typically formulated for administration with a pharmaceutically acceptable carrier or diluent. For example, solid oral forms may contain, together with the active compound(s), diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

Preferably, the anti-HCV benzodiazepines of the formula (I) are solubilised in a carrier containing (a) a pharmaceutically acceptable oil selected from esterification or polyether products of glycerides with vegetable oil fatty acids of chain length $C_8$-$C_{10}$ and (b) a pharmaceutically acceptable surfactant selected from oleate and laurate esters of a polyalcohol copolymerized with ethylene oxide. Particularly preferred carriers contain Labrafil as the oil and Tween 20 or Tween 80 as the surfactant.

The anti-HCV benzodiazepines of the formula (I) may also be suspended in PEG 400 for oral administration.

A therapeutically effective amount of an anti-HCV benzodiazepine of the invention is administered to a patient. A typical dose is from about 0.001 to 50 mg, typically 0.5 to 30 mg, preferably 1 to 20 mg active ingredient per kg of body weight, according to the activity of the specific composition, the age, weight and conditions of the subject to be treated, the type and severity of the disease and the frequency and route of administration. Preferably, daily dosage levels are from 5 mg to 2 g active ingredient.

The following Examples illustrate the invention. They do not however, limit the invention in any way. In this regard, it is important to understand that the particular assays used in the Examples section are designed only to provide an indication of antiviral activity. There are many assays available to determine the activity of given compounds against HCV, and a negative result in any one particular assay is therefore not determinative.

EXAMPLES

In this section, all temperatures are in ° C. Flash column chromatography was carried out using Merck 9385 silica. Solid phase extraction (SPE) chromatography was carried out using Jones Chromatography (Si) cartridges under 15 mmHg vacuum with stepped gradient elution. Thin layer chromatography (TLC) was carried out on plastic plates.

LC-MS Conditions

Samples were run on a MicroMass ZMD, using electrospray with simultaneous positive-negative ion detection.

Column: YMC-PACK FL-ODS AQ, 50×4.6 mm I.D S-5 µm.

Gradient: 95:5 to 5:95 v/v $H_2O$/$CH_3CN$+0.05% Formic Acid over 4.0 min, hold 3 min, return to 95:5 v/v $H_2O$/$CH_3CN$+0.05% Formic Acid over 0.2 min and hold at 95:5 v/v $H_2O$/$CH_3CN$+0.05% Formic Acid over 3 min.

Detection: PDA 250-340 nm.

Flow rate: 1.5 ml/min

Intermediate 1

Benzotriazol-1-yl-benzyloxycarbonylamino-acetic acid

A mixture of glyoxylic acid monohydrate (4.60 g), benzotriazole (5.95 g) and benzyl carbamate (7.55 g) was heated to reflux in toluene (100 ml) for 18 h, under Dean-Stark conditions. The mixture was then allowed to cool to room temperature, and the resulting precipitate collected by filtration. This was then recrystallised from diethyl ether giving an off-white solid (11.66 g)

$^1$H NMR (d6 DMSO, δ) 5.07 (q+s, 3H) 7.25 (d, 1H) 7.3-7.63 (m, 6H) 7.92-8.10 (m, 2H) 9.32 (d, 1H)

LC/MS Found ES−=325 RT=4.68 min

Intermediate 2

[Benzotriazol-1-yl(2-(4-chloro-benzoyl)-phenylcarbamoyl)-methyl]-carbamic acid benzyl ester A cold (0° C.) solution of Intermediate 1 (7.2 g) in dry THF (100 ml) under nitrogen was stirred, and was treated dropwise with a solution of oxalyl chloride (4.4 g) in dry dichloromethane (50 ml), followed by dry dimethylformamide (2 ml). This resulting mixture was stirred for 2 h, and was then treated with a solution This was added to a stirred solution of (2-aminophenyl)-4-chlorophenyl-methanone (3.48 g) and N-methylmorpholine (3.1 g) in THF (40 ml) at 0° C. After addition the mixture was allowed to warm to room temperature, and was stirred for 1 h. The precipitate was removed by filtration, and the solvent evaporated giving a gummy solid, which was used without purification or characterisation.

Intermediate 3

(2-oxo-5-(4-chloro)-phenyl-2,3-dihydro-1H-benzo[e][1,4]diazepin-3-yl)-carbamic acid benzyl ester A solution of Intermediate 2 in 7M ammonia in methanol (100 ml) was stirred at room temperature for 5 h. The solvent was evaporated, and the residue partitioned between ethyl acetate, and 1M sodium hydroxide. The dried organic layer was evaporated, and the residue dissolved in acetic acid (200 ml) containing ammonium acetate (5.8 g). The resulting mixture was stirred at room temperature for 18 h, and then the solvent was evaporated. The residue was dissolved in water and ethyl acetate, and the pH was adjusted to ca.8 with sodium hydroxide. The dried organic extracts were evaporated, and the residue triturated with diethyl ether giving a beige solid (3.1 g).

LC/MS Found ES+=420,422 ($C_{23}H_{13}ClN_3O_3$=419.5)

Intermediate 4

3-Amino-5-(4-chloro-phenyl)-1,3-dihydro-benzo[e][1,4]diazepin-2-one

A solution of Intermediate 3 (3.25 g) in 45% hydrogen bromide in acetic acid (85 ml) was heated to 70° C. for 2 h. The mixture was then allowed to cool, and was diluted with diethyl ether. The hydrobromide salt of the title compound was obtained by filtration and dried, giving a bright yellow solid (2.2 g)

NMR (δ, d6 DMSO) 5.18 (d, 1H) 7.32 (d, 1H) 7.40 (d, 1H) 7.47-7.53 (m, 5H) 7.77 (dd, 1H) 9.07 (br s, 2H) 11.41 (s, 1H)

Intermediate 5

{1-[5-(4-Chloro-phenyl)-2-oxo-2,3-dihydro-1H-benzo[e][1,4]diazepin-3-lcarbamoyl]-2-phenyl-ethyl}-carbamic acid tert-butyl ester A solution of Intermediate 4 (1.3 g) in dry THF was treated with triethylamine, O-(Benzotriazol-1-yl)-N—N—N',N'-tetramethyluronium hexafluorophosphate and Boc-D-phenylalanine. The mixture was stirred at room temperature for 5 h under nitrogen. The mixture was then partitioned between DCM and 1M potassium carbonate solution. The organic layer was dried and concentrated to yield product as a crude black residue (4.5 g) which after LC-MS was taken on crude to the next step.

LC/MS RT=2.89 min, Found ES+=533.07 ($C_{29}H_{29}ClN_4O_4$=533.03)

Preparation Intermediates 6 and 7

Enantiomers of 2-Amino-N-[5-(4-chloro-phenyl)-2-oxo-2,3-dihydro-1H-benzo[e][1,4]diazepin-3-yl]-3-phenyl-propionamide Intermediate 5 (crude 4.5 g) was treated with 2M HCl in diethyl ether solution and stirred at room temperature for 16 h overnight. Solvent was then removed in vacuo and the two enantiomers separated by column chromatography (800:8:1 DCM:EtOH:NH$_3$) to yield title compounds as pale yellow solids 6 (360 mg) and 7(205 mg).

Intermediate 6 (R isomer) LC/MS RT=2.10 min, Found ES+=432.98 ($C_{24}H_{21}ClN_4O_2$=432.91)

$^1$H NMR (CDCl$_3$, δ) 2.76 (dd, 1H) 3.29 (dd, 1H) 3.66 (m, 1H) 5.49 (d, 1H) 7.11 (d, 2H) 7.19-7.30 (m, 8H) 7.46 (m, 3H) 8.34 (s, 1H) 8.85 (d, 1H)

Intermediate 7 (S isomer) LC/MS RT=2.23 min, Found ES+=432.97 ($C_{24}H_{21}ClN_4O_2$=432.91)

$^1$H NMR (CDCl$_3$, δ) 2.76 (dd, 1H) 3.29 (dd, 1H) 3.66 (m, 1H) 5.49 (d, 1H) 7.09 (d, 2H) 7.16-7.30 (m, 8H) 7.43 (m, 3H) 8.05 (s, 1H) 8.83 (d, 1H)

Preparation Intermediates 8 and 9

Enantiomers of N-[5-(4-Chloro-phenyl)-2-oxo-2,3-dihydro-1H-benzo[e][1,4]diazepin-3-yl]-3-phenyl-2-(3-phenyl-thioureido)-propionamide To each intermediate 6 (360 mg) and 7 (205 mg) in dry DCM was added phenylisothiocyanate and the mixtures were stirred at room temperature under nitrogen for 15 h overnight. The solvent was then removed under reduced pressure to yield yellow residues. These were each dissolved in a minimal quantity of DCM and precipitated with petroleum ether. The mixtures were filtered to yield title compounds as off white solids 8 (420 mg) and 9 (302 mg).

Intermediate 8 (R isomer) LC/MS RT=2.86 min, Found ES+=568.07 ($C_{31}H_{26}ClN_5O_2S$=568.10)

$^1$H NMR (CDCl$_3$, δ) 3.36 (m, 2H) 5.37 (d, 2H) 6.65 (d, 1H) 6.97 (d, 2H) 7.10-7.29 (m, 13H), 7.39 (d, 2H) 7.48 (t, 2H) 7.84 (s, 1H) 8.65 (s, 1H)

Intermediate 9 (S isomer) LC/MS RT=2.90 min, Found ES+=568.09 ($C_3H_{26}ClN_5O_2S$=568.10)

$^1$H NMR (CDCl$_3$, δ) 3.27 (m, 2H) 5.37 (d, 1H) 5.53 (q, 1H) 6.72 (d, 1H) 6.97 (d, 2H) 7.13-7.33 (m, 14H), 7.45 (d, 2H) 7.63 (s, 1H) 8.85 (s, 1H) 8.67 (s, 1H)

Preparation Intermediates 10 and 11

Enantiomers of 3-Amino-5-(4-chloro-phenyl)-1,3-dihydro-benzo[e][1,4]diazepin-2-one Each intermediate 8 (420 mg) and 9 (302 mg) was treated with 2M HCl in diethyl ether solution and stirred at room temperature for 16 h overnight. Solvent was then removed in vacuo to yield pale yellow residues. These were each dissolved in a minimal quantity of DCM and precipitated with petroleum ether. The mixtures were filtered to yield title compounds as off-white solids 10 (303 mg) and 11 (118 mg).

Intermediate 10 (R isomer) LC/MS RT=1.98 min, Found ES+=285.92 ($C_{15}H_{12}ClN_3O$=285.74)

$^1$H NMR (MeOD, δ) 4.94 (s, 1H) 7.28-7.52 (m, 5H) 7.61-7.71 (m, 3H) 9.55 (br s, 2H) 11.20 (s, 1H)

Intermediate 11 (S isomer) LC/MS RT=1.97 min, Found ES+=285.90 ($C_{15}H_{12}ClN_3O$=285.74)

$^1$H NMR (MeOD, δ) 4.75 (s, 1H) 6.54 (d, 1H) 6.95-7.20 (m, 5H) 7.31 (d, 2H) 9.15 (br s, 2H) 10.81 (s, 1H)

Example 1

N-[5-(4-Chloro-phenyl)-2-oxo-2,3-dihydro-1H-benzo[e][1,4]diazepin-3-yl]-2-ethoxy-benzamide To a solution of intermediate 4 (30 mg) in DMF (1 ml) was added triethylamine (22 µl), O-benzotriazol-1-yl-N,N,N',N'- tetramethyluronium hexafluorophosphate (40 mg) and 2-ethoxybenzoic acid (20 mg). This mixture was stirred at room temperature for 18 h under nitrogen. Product was precipitated by the addition of water and this was filtered off and purified by preparative HPLC to yield title compound (11 mg) as a white solid.
LC/MS RT=2.80 min, Found ES+=434.02 ($C_{24}H_{20}ClN_3O_3$=433.90)
NMR (δ, d6 DMSO) 1.56 (t, 3H) 4.30 (q, 2H) 5.43 (d, 1H) 7.11 (t, 1H) 7.25-7.41 (m, 4H)) 7.51-7.55 (m, 5H) 7.66 (t, 1H) 8.02 (dd, 1H) 9.77 (d, 1H)

Example 2

(S)—N-[5-(4-Chloro-phenyl)-2-oxo-2,3-dihydro-1H-benzo[e][1,4]diazepin-3-yl]-2-ethoxy-benzamide To a solution of intermediate 11 (30 mg) in DMF (1 ml) was added triethylamine (22 μl), O-benzotriazol-1-yl-N,N,N',N'-tetramethyluronium hexafluorophosphate (40 mg) and 2-ethoxybenzoic acid (18 mg). This mixture was stirred at room temperature for 18 h under nitrogen. Product was precipitated by the addition of water and this was filtered off and purified by preparative HPLC to yield title compound (11 mg) as a white solid.
LC/MS RT=2.80 min, Found ES+=434.02 ($C_{24}H_{20}ClN_3O_3$=433.90)
NMR (δ, d6 DMSO) 1.56 (t, 3H) 4.30 (q, 2H) 5.43 (d, 1H) 7.11 (t, 1H) 7.25-7.41 (m, 4H)) 7.51-7.55 (m, 5H) 7.66 (t, 1H) 8.02 (dd, 1H) 9.77 (d, 1H)

Example 3

N-[5-(4-Chloro-phenyl)-2-oxo-2,3-dihydro-1H-benzo[e][1,4]diazepin-3-yl]-2,5-dimethoxy-benzamide Prepared as for Example 1, from intermediate 4 using 2,5-dimethoxybenzoic acid (23 mg).
LC/MS RT=2.73 min, Found ES+=450.00 ($C_{24}H_{20}ClN_3O_4$=449.90)
NMR (δ, d6 DMSO) 3.83 (s, 3H) 4.08 (s, 3H) 5.49 (d, 1H) 7.25-7.44 (m, 6H)) 7.59 (m, 4H) 7.75 (t, 1H) 9.72 (d, 1H) 11.11 (br s, 1H)

Example 4

(S)—N-[5-(4-Chloro-phenyl)-2-oxo-2,3-dihydro-1H-benzo[e][1,4]diazepin-3-yl]-2,5-dimethoxy-benzamide Prepared as for Example 1, from intermediate 11 using 2,5-dimethoxybenzoic acid (20 mg).
LC/MS RT=2.73 min, Found ES+=450.00 ($C_{24}H_{20}ClN_3O_4$=449.90)
NMR (δ, d6 DMSO) 3.83 (s, 3H) 4.08 (s, 3H) 5.49 (d, 1H) 7.25-7.44 (m, 6H)) 7.59 (m, 4H) 7.75 (t, 1H) 9.72 (d, 1H) 11.11 (br s, 1H)

Example 5

(R)—N-[5-(4-Chloro-phenyl)-2-oxo-2,3-dihydro-1H-benzo[e][1,4]diazepin-3-yl]-2,5-dimethoxy-benzamide Prepared as for Example 1, from intermediate 10 using 2,5-dimethoxybenzoic acid (20 mg).
LC/MS RT=2.74 min, Found ES+=450.01 ($C_{24}H_{20}ClN_3O_4$=449.90)
NMR (δ, d6 DMSO) 3.94 (s, 3H) 4.18 (s, 3H) 5.49 (d, 1H) 7.25-7.44 (m, 6H)) 7.59 (m, 4H) 7.75 (t, 1H) 9.85 (d, 1H) 11.23 (br s, 1H)

Example 6

N-[5-(4-Chloro-phenyl)-2-oxo-2,3-dihydro-1H-benzo[e][1,4]diazepin-3-yl]-5-fluoro-2-methoxy-benzamide Prepared as for Example 1, from intermediate 4 using 5-fluoro-2-methoxybenzoic acid (19 mg).
LC/MS RT=2.77 min, Found ES+=438.01 ($C_{23}H_{17}ClFN_3O_3$=437.86)
NMR (δ, d6 DMSO) 4.25 (s, 3H) 5.63 (d, 1H) 7.51-7.73 (m, 9H)) 7.89 (m, 2H) 9.85 (d, 1H) 11.26 (br s, 1H)

Example 7

(S)—N-[5-(4-Chloro-phenyl)-2-oxo-2,3-dihydro-1H-benzo[e][1,4]diazepin-3-yl]-5-fluoro-2-methoxy-benzamide Prepared as for Example 1, from intermediate 11 using 5-fluoro-2-methoxybenzoic acid (18 mg).
LC/MS RT=2.77 min, Found ES+=438.01 ($C_{23}H_{17}ClFN_3O_3$=437.86)
NMR (δ, d6 DMSO) 4.25 (s, 3H) 5.63 (d, 1H) 7.51-7.73 (m, 9H)) 7.89 (m, 2H) 9.85 (d, 1H) 11.26 (br s, 1H)

Example 8

(R)—N-[5-(4-Chloro-phenyl)-2-oxo-2,3-dihydro-1H-benzo[e][1,4]diazepin-3-yl]-5-fluoro-2-methoxy-benzamide Prepared as for Example 1, from intermediate 10 using 5-fluoro-2-methoxybenzoic acid (18 mg).
LC/MS RT=2.77 min, Found ES+=437.98 ($C_{23}H_{17}ClFN_3O_3$=437.86)
NMR (δ, d6 DMSO) 4.05 (s, 3H) 5.42 (d, 1H) 7.30-7.41 (m, 9H)) 7.68 (m, 2H) 9.64 (d, 1H)

Example 9

5-Chloro-N-[5-(4-chloro-phenyl)-2-oxo-2,3-dihydro-1H-benzo[e][1,4]diazepin-3-yl]-2-methoxy-benzamide Prepared as for Example 1, from intermediate 4 using 5-chloro-2-methoxybenzoic acid (20 mg).
LC/MS RT=2.85 min, Found ES+=453.98 ($C_{23}H_{17}Cl_2N_3O_3$=454.32)
NMR (δ, d6 DMSO) 3.98 (s, 3H) 5.33 (d, 1H) 7.23-7.33 (m, 4H)) 7.44 (m, 4H) 7.56 (m, 2H) 7.82 (d, 1H) 9.50 (d, 1H) 10.98 (br s, 1H)

Example 10

(S)-5-Chloro-N-[5-(4-chloro-phenyl)-2-oxo-2,3-dihydro-1H-benzo[e][1,4]diazepin-3-yl]-2-methoxy-benzamide Prepared as for Example 1, from intermediate 11 using 5-chloro-2-methoxybenzoic acid (20 mg).
LC/MS RT=2.85 min, Found ES+=453.98 ($C_{23}H_{17}Cl_2N_3O_3$=454.32)
NMR (δ, d6 DMSO) 3.98 (s, 3H) 5.33 (d, 1H) 7.23-7.33 (m, 4H)) 7.44 (m, 4H) 7.56 (m, 2H) 7.82 (d, 1H) 9.50 (d, 1H) 10.98 (br s, 1H)

Example 11

(R)-5-Chloro-N-[5-(4-chloro-phenyl)-2-oxo-2,3-dihydro-1H-benzo[e][1,4]diazepin-3-yl]-2-methoxy-benzamide Prepared as for Example 1, from intermediate 10 using 5-chloro-2-methoxybenzoic acid (20 mg).

LC/MS RT=2.86 min, Found ES+=453.98 ($C_{23}H_{17}Cl_2N_3O_3$=454.32)

NMR (δ, d6 DMSO) 3.98 (s, 3H) 5.34 (d, 1H) 7.21-7.31 (m, 4H)) 7.49 (m, 4H) 7.61 (m, 1H) 8.22 (s, 1H) 9.86 (d, 1H) 10.88 (br s, 1H)

Example 12

3-Bromo-thiophene-2-carboxylic acid [5-(4-chloro-phenyl)-2-oxo-2,3-dihydro-1H-benzo[e][1,4]diazepin-3-yl]-amide Prepared as for Example 1, from intermediate 4 using 3-bromothiophene-2-carboxylic acid (22 mg).

LC/MS RT=2.78 min, Found ES+=475.84 ($C_{20}H_{13}BrClN_3O_2S$=474.77)

NMR (δ, d6 DMSO) 5.16 (d, 1H) 7.06-7.13 (m, 4H)) 7.28 (m, 4H) 7.42 (t, 1H) 7.70 (d, 1H) 8.83 (d, 1H) 10.85 (br s, 1H)

Example 13

(S)-3-Bromo-thiophene-2-carboxylic acid [5-(4-chloro-phenyl)-2-oxo-2,3-dihydro-1H-benzo[e][1,4]diazepin-3-yl]-amide Prepared as for Example 1, from intermediate 11 using 3-bromothiophene-2-carboxylic acid (22 mg).

LC/MS RT=2.78 min, Found ES+=475.84 ($C_{20}H_{13}BrClN_3O_2S$=474.77)

NMR (δ, d6 DMSO) 5.16 (d, 1H) 7.06-7.13 (m, 4H)) 7.28 (m, 4H) 7.42 (t, 1H) 7.70 (d, 1H) 8.83 (d, 1H) 10.85 (br s, 1H)

Activity Example

Polymerase 96 Well Microtitre Plate Based $IC_{50}$ Assay

Principle

Inhibitors of HCV Polymerase can be detected radioactively by monitoring the incorporation of $^{33}P$-UTP within an RNA template/Bi-primer system using streptavidin coated FlashPlates. The template and primer for the reaction can be bought externally from Amersham (Poly A) and MWG-Dharmacon (Biotinylated-$U_{13}$). The cold UTP can be purchased from Roche and the HCV Polymerase was expressed and purified by Prof Alistair Hawkins at Newcastle University, UK.

Procedure

2 Preparation of Reagents

50 µl substrate, 40 µl enzyme, 10 µl compound=100 µl assay 2.1 Preparation of $IC_{50}$ Dilution Plates Compounds are diluted so that DMSO remains 10% at all times. E.g. 5 µl compound (10 mM)+5 µl DMSO+90 µl Buffer (see below for buffer)

|   | 1 | 2 | 3 | 4 | 5 | 6 | 7 | 8 | 9 | 10 | 11 | 12 |
|---|---|---|---|---|---|---|---|---|---|----|----|----|
| A |   |   | 500 | 500 | 500 | 500 | 500 | 500 | 500 | 500 | 500 | 500 |
| B |   |   | 250 | 250 | 250 | 250 | 250 | 250 | 250 | 250 | 250 | 250 |
| C |   |   | 125 | 125 | 125 | 125 | 125 | 125 | 125 | 125 | 125 | 125 |
| D |   |   | 62.5 | 62.5 | 62.5 | 62.5 | 62.5 | 62.5 | 62.5 | 62.5 | 62.5 | 62.5 |
| E |   |   | 31.3 | 31.3 | 31.3 | 31.3 | 31.3 | 31.3 | 31.3 | 31.3 | 31.3 | 31.3 |
| F |   |   | 15.6 | 15.6 | 15.6 | 15.6 | 15.6 | 15.6 | 15.6 | 15.6 | 15.6 | 15.6 |
| G |   |   | 7.81 | 7.81 | 7.81 | 7.81 | 7.81 | 7.81 | 7.81 | 7.81 | 7.81 | 7.81 |
| H |   |   | 3.91 | 3.91 | 3.91 | 3.91 | 3.91 | 3.91 | 3.91 | 3.91 | 3.91 | 3.91 |

(concentrations are in µM)

2.2 Reagent Preparation

Some 20 mM Tris-HCl, pH 7.5, 5 mM $MgCl_2$, 25 mM KCL, 3 mM DTT and 0.05% BSA is made up.

Enzyme blank: 40 µl 20 mM Tris-HCl buffer (as above) pH 7.5

Substrate mix (made up immediately before use): 32000 µl Total

Enzyme mix (made up immediately before use): 30000 µl

3 Running the Assay

The PolyA and Biotinylated $U_{13}$ are annealed at 70° C. for 5 minutes to 40 µM $U_{13}$ (212 µg/ml polyA.) and cooled gently on ice prior to use (110 µl primer (80 µM)+5.5 µl poly A+104.5 µl dH20.). Some 200 µl annealed primer/template is mixed with 12.8 µl UTP (1 mM stock), 25.6 µl 33p-UTP and 31761.6 µl Buffer to make the substrate mix.

From $IC_{50}$ dilution plates 10 µl are transferred from column 3 into columns 3 and 3 on two separate assay plates. This is repeated for all compound dilutions to 2 separate assay plates. Then 10 µl 10% DMSO solution is added to positive and negative controls (see plate map below). In addition, 40 µl 20 mM Tris-HCl buffer is added to negative controls.

Then 50 µl substrate mix is added to all wells.

Then 40 µl enzyme mix each is added to all other wells and the reaction is left for 100 minutes shaking at 25° C.

The reaction is terminated with the addition of 100 µl, 100 mM EDTA and the volume is transferred to a streptavidin coated flash plate, covered and left for an hour.

All plates are washed three times in SkanWasher platewasher (Skatron Instruments) under programme 'AH'. The wash buffer contains, 0.01M phosphate buffer, 0.0027M potassium chloride and 0.137M sodium chloride, pH 7.4 at 25° C., 0.05% Tween All plate are recovered and the cpmB read in the TopCount (supplied by DPM solutions), protocol 6.

Assay Concentrations and Optimisation

| Plate Map | | | | | | | | | | | |
|---|---|---|---|---|---|---|---|---|---|---|---|
| +ve ctrl | +ve ctrl | Cmp 1 | Cmp 2 | Cmp 3 | Cmp 4 | Cmp 5 | Cmp 6 | Cmp 7 | Cmp 8 | Cmp 9 | Cmp 10 |
| +ve ctrl | +ve ctrl | Cmp 1 | Cmp 2 | Cmp 3 | Cmp 4 | Cmp 5 | Cmp 6 | Cmp 7 | Cmp 8 | Cmp 9 | Cmp 10 |
| +ve ctrl | +ve ctrl | Cmp 1 | Cmp 2 | Cmp 3 | Cmp 4 | Cmp 5 | Cmp 6 | Cmp 7 | Cmp 8 | Cmp 9 | Cmp 10 |
| −ve ctrl | −ve ctrl | Cmp 1 | Cmp 2 | Cmp 3 | Cmp 4 | Cmp 5 | Cmp 6 | Cmp 7 | Cmp 8 | Cmp 9 | Cmp 10 |
| −ve ctrl | −ve ctrl | Cmp 1 | Cmp 2 | Cmp 3 | Cmp 4 | Cmp 5 | Cmp 6 | Cmp 7 | Cmp 8 | Cmp 9 | Cmp 10 |
| −ve ctrl | −ve ctrl | Cmp 1 | Cmp 2 | Cmp 3 | Cmp 4 | Cmp 5 | Cmp 6 | Cmp 7 | Cmp 8 | Cmp 9 | Cmp 10 |
| Std | Std | Cmp 1 | Cmp 2 | Cmp 3 | Cmp 4 | Cmp 5 | Cmp 6 | Cmp 7 | Cmp 8 | Cmp 9 | Cmp 10 |
| | | Cmp 1 | Cmp 2 | Cmp 3 | Cmp 4 | Cmp 5 | Cmp 6 | Cmp 7 | Cmp 8 | Cmp 9 | Cmp 10 |

+ve ctrl = 50 µl substrate mix 40 µl polymerase mix, 10 µl DMSO (10%)
−ve ctrl = 50 µl substrate mix, 40 µl Tris-HCl buffer pH 7.5, 10 µl DMSO (10%)
Cmp = 50 µl substrate mix, 40 µl HCV Polymerase mix, 10 µl of 10% DMSO test compound
Std = 50 µl substrate mix, 40 µl 20 mM Tris-HCl buffer, 10 µl of 10% DMSO standard compound

| RESULTS | |
|---|---|
| Example | IC50, * >1 µM, ** <1 µM |
| 1 | * |
| 2 | * |
| 3 | ** |
| 4 | ** |
| 5 | * |
| 6 | * |
| 7 | * |
| 8 | * |
| 9 | ** |
| 10 | ** |
| 11 | * |
| 12 | * |

The invention claimed is:

1. A compound of formula (Ib'):

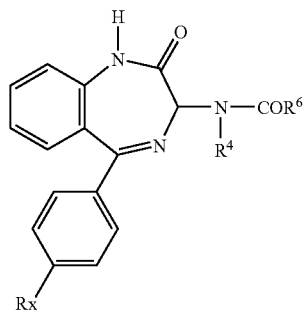

(Ib')

a pharmaceutically acceptable salt, or a mixture thereof, wherein:
Rx is chlorine; and
$R^6$ is 1) a phenyl substituted by 1 $C_1$-$C_2$ alkoxy, and optionally further substituted by one additional $C_1$-$C_2$ alkoxy or halogen atom; or 2) a thiophenyl substituted by one halogen.

2. The compound according to claim 1, wherein the benzodiazepine derivative of formula (Ib') is:
N-[5-(4-Chloro-phenyl)-2-oxo-2,3-dihydro-1H-benzo[e][1,4]diazepin-3-yl]-2-ethoxy-benzamide;
(S)—N-[5-(4-Chloro-phenyl)-2-oxo-2,3-dihydro-1H-benzo[e][1,4]diazepin-3-yl]-2-ethoxy-benzamide;
N-[5-(4-Chloro-phenyl)-2-oxo-2,3-dihydro-1H-benzo[e][1,4]diazepin-3-yl]-2,5-dimethoxy-benzamide;
(S)—N-[5-(4-Chloro-phenyl)-2-oxo-2,3-dihydro-1H-benzo[e][1,4]diazepin-3-yl]-2,5-dimethoxy-benzamide;
(R)—N-[5-(4-Chloro-phenyl)-2-oxo-2,3-dihydro-1H-benzo[e][1,4]diazepin-3-yl]-2,5-dimethoxy-benzamide;
N-[5-(4-Chloro-phenyl)-2-oxo-2,3-dihydro-1H-benzo[e][1,4]diazepin-3-yl]-5-fluoro-2-methoxy-benzamide;
(S)—N-[5-(4-Chloro-phenyl)-2-oxo-2,3-dihydro-1H-benzo[e][1,4]diazepin-3-yl]-5-fluoro-2-methoxy-benzamide;
(R)—N-[5-(4-Chloro-phenyl)-2-oxo-2,3-dihydro-1H-benzo[e][1,4]diazepin-3-yl]-5-fluoro-2-methoxy-benzamide;
5-Chloro-N-[5-(4-chloro-phenyl)-2-oxo-2,3-dihydro-1H-benzo[e][1,4]-diazepin-3-yl]-2-methoxy-benzamide;
(S)-5-Chloro-N-[5-(4-chloro-phenyl)-2-oxo-2,3-dihydro-1H-benzo[e][1,4]-diazepin-3-yl]-2-methoxy-benzamide;
(R)—N-[5-(4-Chloro-phenyl)-2-oxo-2,3-dihydro-1H-benzo[e][1,4]diazepin-3-yl]-5-fluoro-2-methoxy-benzamide;
3-Bromo-thiophene-2-carboxylic acid [5-(4-chloro-phenyl)-2-oxo-2,3-dihydro-1H-benzo[e][1,4]diazepin-3-yl]-amide; or
(S)-3-Bromo-thiophene-2-carboxylic acid [5-(4-chloro-phenyl)-2-oxo-2,3-dihydro-1H-benzo[e][1,4]diazepin-3-yl]-amide,
a pharmaceutically acceptable salt, or mixture thereof.

3. The compound (S)—N-[5-(4-Chloro-phenyl)-2-oxo-2,3-dihydro-1H-benzo[e][1,4]diazepin-3-yl]-5-fluoro-2-methoxy-benzamide, a pharmaceutically acceptable salt or a mixture thereof.

4. A pharmaceutical composition comprising a compound according to claim 1, 2 or 3, and a pharmaceutically acceptable carrier or diluent.

* * * * *